United States Patent [19]

Johnson et al.

[11] 4,055,409

[45] Oct. 25, 1977

[54] PYRAZOLE PLANT GROWTH REGULANTS

[75] Inventors: Alexander L. Johnson; Philip B. Sweetser, both of Wilmington, Del.

[73] Assignee: E. I. Du Pont de Nemours and Company, Wilmington, Del.

[21] Appl. No.: 627,462

[22] Filed: Oct. 30, 1975

Related U.S. Application Data

[60] Division of Ser. No. 397,720, Sept. 17, 1973, Pat. No. 3,948,937, which is a continuation-in-part of Ser. No. 230,508, Feb. 29, 1972, abandoned, which is a continuation-in-part of Ser. No. 136,576, April 22, 1971, abandoned.

[51] Int. Cl.$^2$ .............................................. A01N 5/00
[52] U.S. Cl. .......................................... 71/76; 71/86; 71/88; 71/90; 71/92

[58] Field of Search ................. 71/92, 76; 260/310 R, 260/311

[56] References Cited

U.S. PATENT DOCUMENTS

| | | | |
|---|---|---|---|
| 3,407,206 | 10/1968 | Bousquet | 71/92 |
| 3,409,425 | 11/1968 | Bousquet | 71/92 |
| 3,700,689 | 10/1972 | McKusick | 260/310 R |

Primary Examiner—Glennon H. Hollrah

[57] ABSTRACT

Substituted pyrazole compounds have been found to be effective plant growth regulants. Exemplary of the effective compounds are 3-(2-carboxyphenyl)-5-phenylpyrazole, its 2-ethanolamine salt, and 3-(2-carboxy-1-cyclohexen-1-yl)-5-phenylpyrazole.

24 Claims, No Drawings

PYRAZOLE PLANT GROWTH REGULANTS

CROSS REFERENCE TO RELATED APPLICATIONS

This application is a division of application Ser. No. 397,720, filed Sept. 17, 1973, now U.S. Pat. No. 3,948,937, which is a continuation-in-part of application Ser. No. 230,508, filed Feb. 29, 1972, now abandoned, which is a continuation-in-part of application Ser. No. 136,576, filed Apr. 22, 1971, now abandoned.

BACKGROUND OF THE INVENTION

Several types of compounds have been found to be useful in modifying or controlling the growth of plants. 2-Substituted pyrazoloisoindolones taught in U.S. Pat. Nos. 3,407,206 and 3,409,425 exhibit this property. Similarly, British 1,022,655 teaches the use of phenoxyacyl pyrazoles as plant growth regulants. Neither of these references suggest the novel pyrazoles of this invention.

SUMMARY OF THE INVENTION

This invention relates to compounds of the formula:

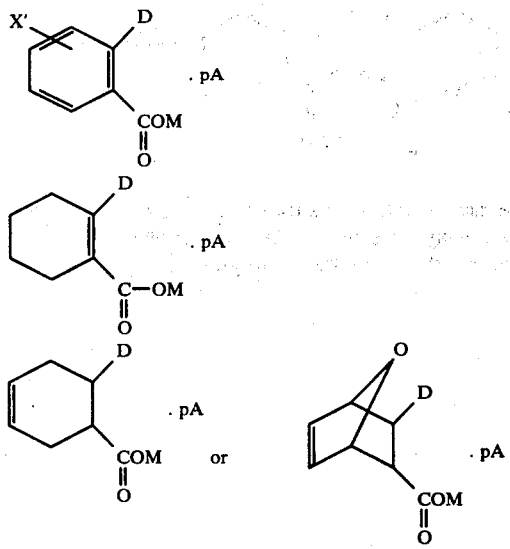

where D is

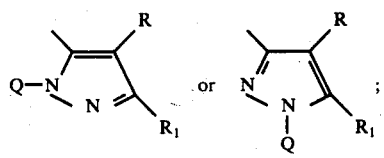

X' is hydrogen, fluorine, chlorine, bromine or methyl;
R is hydrogen or a group selected from —CH$_2$—, —CH$_2$CH$_2$—, and —CH=CH— which joins the 4-position of the pyrazole ring with the 2-position of the R$_1$ substituent;
R$_1$ is sec-alkyl of three to six carbon atoms, tert-alkyl of four to six carbon atoms, cycloalkyl of five or six carbon atoms, naphthyl, biphenylyl, 2-furyl, 2-thienyl, pyridyl, 3-indolyl, or

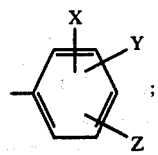

where
X is hydrogen, halogen, alkyl of one to four carbon atoms, hydroxy, alkoxy of one to four carbon atoms, alkylthio of one to four carbon atoms, alkylsulfonyl of one to four carbon atoms, trifluoromethyl or nitro;
Y is hydrogen, chlorine, bromine, methoxy or methyl; and
Z is hydrogen, chlorine, or methyl;
Q is hydrogen, alkyl of one to four carbon atoms, alkanoyl of one to four carbon atoms, alkoxycarbonyl of two to five carbon atoms, or benzenesulfonyl optionally substituted with chlorine or one or two methyls;
M is hydrogen, benzyl, alkyl of one to six carbon atoms, hydroxyalkyl of two or three carbon atoms, alkoxyalkyl of three to five carbon atoms, sodium, potassium, lithium, calcium, magnesium, or

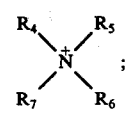

where
R$_4$, R$_5$ and R$_6$ are each independently hydrogen, alkyl of one to four carbon atoms or hydroxyalkyl of two to four carbon atoms; and
R$_7$ is hydrogen, alkyl of one to twelve carbon atoms or benzyl;
p is 0 or 1; and
A is HCl, H$_2$SO$_4$, HNO$_3$ or H$_3$PO$_4$
with the provisos that:
1. when M is other than hydrogen, benzyl or optionally substituted alkyl, p is 0; and
2. the total number of carbon atoms in X, Y, and Z cannot exceed 4.

The invention also relates to compositions containing these compounds and the use of the compounds and compositions as plant growth regulants.

DESCRIPTION OF THE PREFERRED EMBODIMENTS

Of the class of compounds described above, compounds which are particularly preferred due to their plant growth regulant activity are those compounds where R$_1$ is p-methoxyphenyl, p-tolyl, p-chlorophenyl, or phenyl.

More preferred are the compounds of the preferred scope where M is hydrogen, alkali metal or optionally substituted ammonium and R is hydrogen.

PREPARATION

The compounds of this invention can be prepared by opening the appropriately substituted fused-ring compounds, pyrazolo[5,1-a]isoindol-8-ones at the number eight carbon. The use of methanol for this ring-opening reaction, which results in the formation of the corresponding 5-(2-carbomethoxyphenyl)pyrazoles is illustrated below:

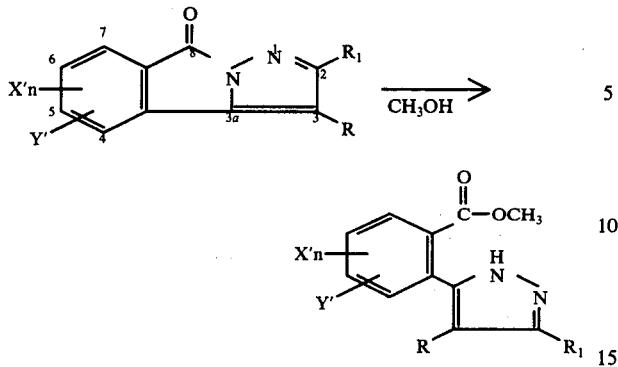

The preparation of the 3,3a-dihydropyrazolo[5,1-a]isoindol-8-ones is taught in U.S. Pat. No. 3,407,206. These compounds can be reacted with dehydrogenating agents such as oxygen, iodine, or 2,3-dichloro-5,6-dicyanobenzoquinone (DDQ) to produce the pyrazolo[5,1-a]isoindol-8-ones as taught in U.S. Pat. No. 3,700,689.

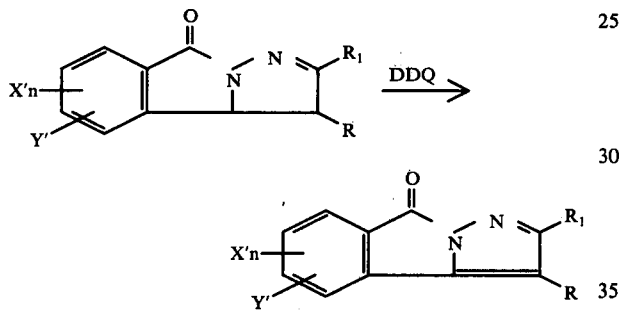

Substituents such as alkyl, alkanoyl, alkoxycarbonyl and arylsulfonyl can be placed on the nitrogens of the ring-opened pyrazole with the appropriate alkyl, alkanoyl, alkoxycarbonyl, or arylsulfonyl halide or dialkyl sulfate in the presence of sodium hydride.

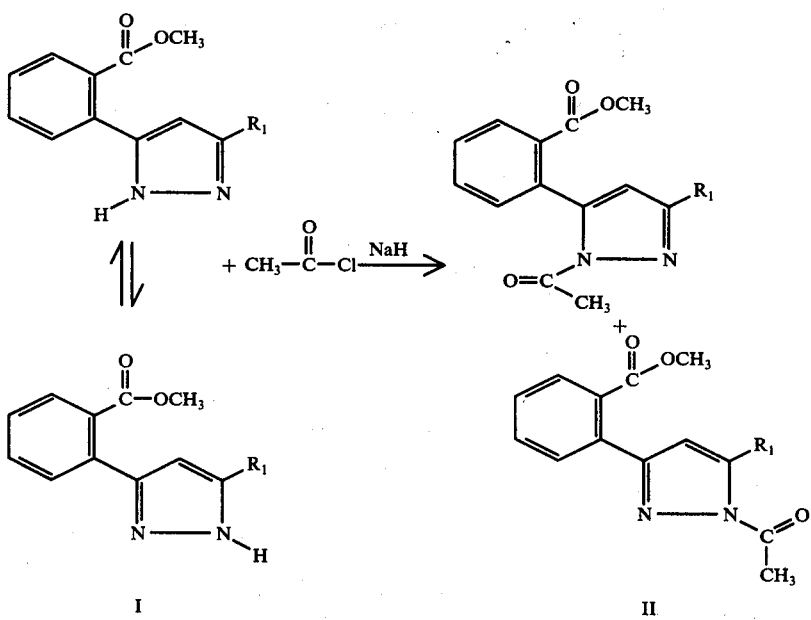

The existence of isomers such as shown above in which the substituent is located on either of the nitrogen atoms is recognized and is a result of the rapid interconversion of the isomeric forms present when Q is hydrogen. For convenience the compounds are named in this invention as though they are solely like type I (or II) above. This invention is intended to include both isomers as they occur.

An alternative synthesis involves treating the disodium salt of the condensation product of a phthalic acid monoester and an acetophenone with hydrazine and one equivalent of mineral acid.

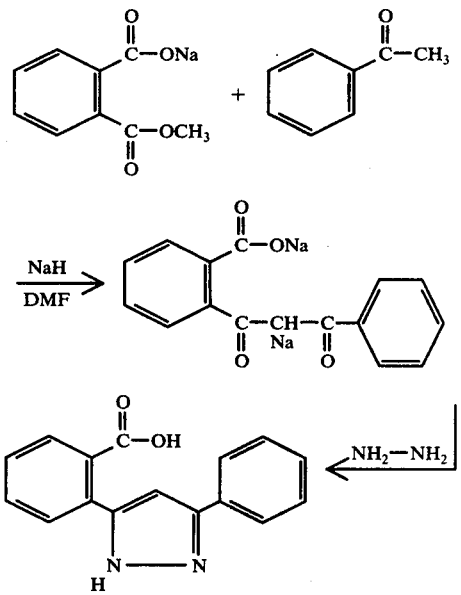

The use of alkyl-substituted hydrazines in place of hydrazine hydrate in the above procedure provides a general synthesis for the N-alkylpyrazoles.

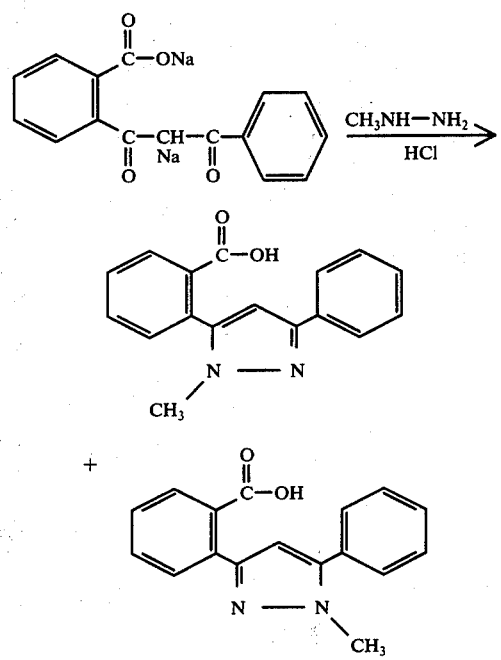

As in the procedure above, the substituents at the 2 position of the phenyl group can be modified by known-type reactions. Similarly, other substituents can be placed on the nitrogen of the pyrazole ring as set out above. Use of substituted phthalic anhydride or ketones other than acetophenone gives the final product having the desired substituents.

Many acids form addition compounds with the pyrazoles of this invention. Preferred acids are halogenated aliphatic acids containing from 2 to 5 carbon atoms, halogenated benzoic acids, halogenated phenylacetic acids, halogenated phenoxyacetic acids, organic sulfonic acids, organic phosphoric acids, and inorganic phosphoric acids. These acids are preferred because the pyrazole addition compounds formed from them are highly phytotoxic and show good oil-solubility. Illustrative of these acids are:

2,3,5-trichlorobenzoic acid
2,3,6-trichlorobenzoic acid
2,3,5,6-tetrachlorobenzoic acid
2,3,5-triiodobenzoic acid
2-methoxy-3,6-dichlorobenzoic acid
2-methoxy-3,5,6-trichlorobenzoic acid
2-methyl-3,6-dichlorobenzoic acid
2,5-dichloro-3-aminobenzoic acid
2,5-dichloro-3-nitrobenzoic acid
2,3,6-trichlorophenylacetic acid
2,3,5,6-tetrachlorophenylacetic acid
2-methoxy-3,6-dichlorophenylacetic acid
2,4-dichlorophenoxyacetic acid
2,4,5-trichlorophenoxyacetic acid
phosphoric acid
methanephosphoric acid
phenylphosphoric acid Most preferred because of the grass-killing power and ease of preparation of their addition compounds are acids of the formula

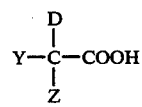

wherein D is halogen; Y is hydrogen, halogen, alkyl of from 1 to 3 carbon atoms, or haloalkyl; and Z is hydrogen, halogen or alkyl of 1 to 3 carbon atoms.

Illustrative of these acids are:

chloroacetic acid
dichloroacetic acid
trichloroacetic acid
bromoacetic acid
dibromoacetic acid
tribromoacetic acid
trifluoroacetic acid
$\alpha,\alpha$-dichloropropionic acid
$\alpha,\alpha$-dibromopropionic acid
$\alpha,\alpha,\beta$-trichloropropionic acid
$\alpha,\alpha,\beta$-trifluoropropionic acid
$\alpha,\alpha$-dichlorobutyric acid
$\alpha,\beta$-dichloroisobutyric acid
$\alpha,\beta\beta$-trichloroisobutyric acid
$\alpha\alpha$-dichlorovaleric acid Also preferred because of the high activity of their pyrazole addition compounds as foliage sprays are acids of the formula $R_5SO_3H$, where $R_5$ is an aliphatic hydrocarbon radical, an aromatic hydrocarbon radical, or a halogen- or alkyl-substituted aromatic hydrocarbon radical.

Illustrative of these acids are:

methanesulfonic acid
ethanesulfonic acid
dodecylsulfonic acid
benzenesulfonic acid
p-toluenesulfonic acid
dodecylbenzenesulfonic acid
2,4,6-trichlorobenzenesulfonic acid
naphthalene-$\beta$-sulfonic acid

COMPOSITIONS

Compositions of this invention comprise a compound of this invention together with one or more surface-active agents.

The surface-active agent used in this invention can be a wetting, dispersing or an emulsifying agent which will assist dispersion of the compound. The surface-active agent or surfactant can include such anionic, cationic and nonionic agents as have heretofore been generally employed in plant-control compositions of similar type. Suitable surface-active agents are set out, for example, in Searle U.S. Pat. No. 2,426,417; Todd U.S. Pat. No. 2,655,447; Jones U.S. Pat. No. 2,412,510; or Lenher U.S. Pat. 2,139,276. A detailed list of such agents is set forth in "Detergents and Emulsifiers Annual" (1969) by John W. McCutcheon, Inc.

Suitable surface-active agents for use in compositions of the present invention are: polyethylene glycol fatty acid esters and fatty alkylol amide condensates, alkylarylsulfonates, fatty alcohol sulfates, dialkyl esters of sodium sulfosuccinate, fatty acid esters of sodium isethionate, polyoxyethylene ethers and thioethers and long-chain quaternary ammonium chloride compounds.

Surface-active dispersing agents such as salts of lignin sulfonic acids, low-viscosity methyl cellulose, polymerized sodium salts of alkylnaphthalenesulfonic acids are also suitable in the herbicidal compositions of this invention.

Among the more preferred surfactants are the anionic and nonionic type. Among the anionic surface-active agents, preferred ones are alkali metal or amine salts of alkylbenzenesulfonic acids such as dodecylbenzenesulfonic acid, sodium lauryl sulfate, alkylnaphthalenesulfonates, sodium N-methyl-N-oleoyltaurate, oleic acid ester of sodium isethionate, dioctyl sodium sulfosuccinate, sodium dodecyldiphenyloxide disulfonate. Among the nonionic compounds, preferred members are alkylphenoxy poly (ethyleneoxy)ethanols such as nonylphenol adducts with ethylene oxide; polyethylene oxide adducts to long-chain aliphatic alcohols such as trimethylnonyl polyethylene glycol ethers, polyethylene oxide adducts of fatty and rosin acids, long-chain alkyl mercaptan adducts with ethylene oxide and polyethylene oxide adducts with sorbitan fatty acid esters.

In general, less than 10% by weight of the surface-active agents will be used in compositions of this invention and ordinarily the amount of surface-active agents will range from 1–5% but may even be less than 1% by weight.

Additional surface-active agents can be added to the above formulation to increase the ratio of surface-active agent: active agent up to as high as 5:1 by weight. Normally the purpose of adding higher amounts of surfactant is to increase the growth regulant effect of the active compounds. When used at higher rates it is preferred that the surfactant be present in the range of one fifth to five parts surfactant for each one part of active agent.

Plant growth regulant compositions of this invention can contain, in addition to a surfactant, finely divided inert diluents such as talcs, natural clays including attapulgite clay and kaolinite clay, pyrophyllite, diatomaceous earths, synthetic fine silicas, calcium silicate, carbonates, calcium phosphates, sulfur, lime and such flours as walnut shell, wheat, redwood, soybean and cottonseed.

Preferred diluents are clays of hydrated aluminum silicate, hydrated aluminum magnesium silicate and hydrated aluminum magnesium iron silicate.

The amount of the finely divided inert solid diluent cam vary widely but will generally range from 10 to 98% by weight of the growth retardant composition. The particle size can vary considerably but will ordinarily be somewhat under 50 microns in the finished formulation. Such compositions are prepared by blending the ingredients and grinding in a hammer mill or an air attrition mill or similar device. Compositions containing a surface-active agent and a solid inert diluent are preferably wettable powders containing from 25 to 90% of a pyrazole.

The pyrazoles of this invention can also be formulated as high strength compositions in which the active ingredient can be present in amounts ranging from 90–99%. The remainder of the composition comprises surface-active agents, preferably in amounts of from 0.2 to 2% and diluents, as described above. Such compositions are prepared by blending and grinding the ingredients to obtain a homogeneous powder of fine particle size.

Compositions of these plant growth regulants and inert solid diluents can also be formulated into granules and pellets. In such compositions, the diluent will generally range from 65 to 99% and the active ingredient can range from 1 to 35%. It should be understood that it will not be necessary to include a surfactant in the granular and pelletized composition. To prepare granules the pyrazole can be dissolved in a solvent, and this solution can be sprayed over pre-formed clay granules, expanded vermiculite or the like, while agitating the mixture to distribute the active ingredient over and throughout the granular mass. Such granules can range in particle size of from +60 mesh to +4 mesh, and an active ingredient content of 1 to 6% is preferred. Granules of even smaller size can be prepared similarly and are applied from appropriately designed equipment. It is also possible to make such granules by mixing the finely divided diluent and finely divided pyrazoles, for instance by grinding together, and then forming granules by adding water, tumbling and drying the resulting spheres. It is also possible to mix a finely divided pyrazole with granular carriers such as attapulgite or vermiculite and then binding the active ingredient to the carrier by spraying the whole with a non-volatile liquid.

Pellets can be prepared by extruding a mixture which comprises the pyrazole, pelleting clay diluents and water into strands, cutting these, and drying the product. Pellet size can range from 10 mesh to larger shapes such as ⅜ inch cubes. Pellets preferably contain from 5 to 35% of the pyrazole. In addition to the diluents, pelletized and granular compositions can contain additives such as binders, surfactants and the like.

In addition to the formulation described above, suspension concentrates can also be prepared. These formulations are prepared by wet-milling the ingredients; i.e., ball milling or by sand-grinding using the method described in Hochberg U.S. Pat. No. 2,581,414, issued Aug. 19, 1948, or Littler U.S. Pat. No. 3,060,084 issued Oct. 23, 1962. Using the methods described in these patents, fine particles of the active compounds within the scope of this invention will be dispersed evenly in a diluent. Such compositions normally contain from 15 to 50% active ingredient and are characterized by having particles which are substantially less than 5-20 microns in diameter.

Water-extendable oil compositions can also be employed with one or more of the pyrazoles of this invention. In these plant growth regulant compositions, surface-active agents and an oil form a liquid which can be conveniently poured and measured. Such liquid concentrates can be mixed with water at the point of application to form a dilute spray containing the herbicide and the surface-active agent. Such compositions have the advantage that the oil will often act as a foam inhibitor and thus reduce the tendency for large amounts of surfactants to form objectionable foam. These oil formulations are dispersions of the pyrazoles in finely divided form in non-solvent carriers. A non-solvent carrier is an oil in which the pyrazole has low solubility, for instance, less than about 0.1% at 25° C. Many aliphatic hydrocarbons are examples of such non-solvent carriers. The dispersions are prepared by wet-milling the ingredients, for example in a ball mill or sand mill. The solutions are prepared by blending and agitating the ingredients, possibly with application of heat.

In these emulsifiable oil concentrates, the pyrazoles will be present in amounts ranging from 5 to 35% by weight. Precise concentrations of active agent, of course, will depend on the intended use of the composition. Upon mixing with water at the point of application, the oil concentrate will be diluted, so that in the final formulation the active agent will be present in amounts ranging from 0.5% to 2% by weight. It will be understood that emulsifiable compositions will have utility for regulating foliage along highway and railroad rights-of-way, as well as other locations.

It is, of course, also possible to use such oil compositions of pyrazoles by extending them with other oils, for example, diesel oil, herbicidal oil, and the like for applications such as railroad rights-of-way.

Solution formulations can be prepared in organic or mixed organic and aqueous solvents. Solution formulations can often be used for direct low-volume applications. For such formulations, all that is required is practical solubility and stability of the active material in the chosen solvent. An important sub-class of solution formulations is emulsifiable concentrates. In these, a water-immiscible solvent is required as well as a surfactant system to help form and stabilize the aqueous emulsion which the ultimate user will prepare for application.

Still another liquid formulation which is particularly convenient for small scale use is the "aerosol" formulation which is packaged under pressure in a suitable container. The liquid phase may be a suspension, emulsion, or solution. For simplicity in preparation and use, solutions are preferred. The pressure may be supplied by low-boiling liquids such as propane or chlorofluorocarbons, or by relatively insoluble gases such as carbon dioxide or nitrous oxide. The chlorofluorocarbons are preferred for a combination of good solvent power and lack of flammability.

It is preferred that the active ingredient remain totally dissolved in all solution formulations at 0° C or as low a storage temperature as can be reasonably expected for prolonged periods. In order to insure this, co-solvents, which may be water-miscible even in emulsifiable concentrates, may also be included in the formulations.

Organic liquids suitable for preparation of solutions, suspensions and emulsifiable concentrates of the compounds of this invention include alcohols, glycols, cellosolves, carbitols, ketones, esters, sulfoxides, sulfones, sulfamides, amides, paraffinic hydrocarbons, aromatic hydrocarbons and halogenated hydrocarbons. Choice of a liquid is dictated by the solubility of the active compound to be used and whether a suspension or solution is desired. Although many compounds represented by Formula I have poor solubility characteristics, for some applications relatively low concentrations of active ingredient are desirable.

The ranges of active ingredient given in the formulations described above are based on normal commercial practice. There is, of course, no reason why very much more dilute concentrations cannot be made. At the very low rates of active ingredient required for some plant growth effects, the added cost (on an active ingredient basis) of dilute formulations is more than counterbalanced by increased convenience in accurate application. For example, at a use rate of about 0.004 pounds per acre in an ultra-low volume of 1 quart per acre only 0.2% solubility of active ingredient is required. With wettable powders, application of one pound commodity per acre would be considered low, but the same 0.004 pounds active per acre would be delivered by a 0.4% wettable powder. These dilute formulations must be more carefully blended than the more concentrated formulations, but otherwise present no unusual difficulties.

APPLICATION

The compounds of this invention are applied to the plants to be affected. By "application to the plants" is meant both application directly to the plant and application to the immediate area where the plant is growing or will be planted. This includes preemergence and postemergence application. Thus, the application may be directly to the plant or to the soil in which the plant is growing or will be planted.

Low rates of application of the active ingredient from 0.001 to 4 pounds per acre provides a means for regulating the growth of plants; e.g., growth retardation, delayed flowering, parthenocarpic fruit set, increased fruit set, carbohydrate enrichment and control of axillary growth. At higher rates of application, from 0.5 to 10 or more pounds per acre, compounds of this invention exhibit herbicidal activity on some plant species under specific growth conditions. The compound is applied with conventional agricultural equipment and is usually applied in one of the compositions set forth above. The actual rate of active ingredient used, of course, must depend on the particular situation, i.e., the actual plant species, its vigor, the time of year and the condition of the soil. These variations will be well known to one skilled in the art.

UTILITY EXAMPLES

The following examples are provided to more clearly explain this invention. All percentages are by weight unless otherwise indicated. All temperatures are in degrees Centigrade (° C).

EXAMPLE 1

The following formulation is prepared:

| | Percent |
|---|---|
| 3-(2-carbomethoxyphenyl)-5-(4-methoxyphenyl)pyrazole | 40 |
| dioctyl sodium sulfosuccinate | 1.5 |
| sodium ligninsulfonate | 3 |
| low-viscosity methyl cellulose | 1.5 |
| attapulgite | 54 |

The ingredients are thoroughly blended, passed through an air mill to produce an average particle size under 15 microns, reblended, and sifted through a U.S.S. No. 50 sieve (0.3 mm openings) before packaging.

All compounds of the invention may be formulated in the same manner.

A peanut field is treated preemergence with 3-(2-carbomethoxyphenyl)-5-(4-methoxyphenyl)pyrazole formulated as in Example 1 at the rate of one kilogram active ingredient per hectare. A heavy population of mixed annual weeds is controlled without injury to the peanuts.

EXAMPLE 2

| | Percent |
|---|---|
| 3-(2-carbomethoxyphenyl)-5-phenylpyrazole | 25.0 |
| Sodium lauryl sulfate | 0.5 |
| Ca, Mg lignin sulfonate | 1.0 |
| Kaolin clay | 73.5 |

The above components are blended and ground in the manner of the formulation of Example 1.

A suspension of 2 to 4 kilograms of active ingredient of this formulation in 500 liters of water is prepared. This suspension is sprayed uniformly over a hectare of bluegrass turf.

The treatment retards the growth of the grass over an extended period, reducing the mowing necessary to maintain the area. The treatment promotes auxillary bud development on the treated plants making the turf thicker. At the same time, good control of broadleaf weeds is noted.

EXAMPLE 3

|  | Percent |
|---|---|
| 3-(2-carbomethoxyphenyl)-5-(4-methoxyphenyl)-pyrazole | 35.0 |
| Ca, Mg lignin sulfonate | 15.0 |
| Hydrated attapulgite | 1.5 |
| Sodium pentachlorophenate | 0.7 |
| Sodium hydroxide | 0.6 |
| Water | 47.2 |

The active component is first hammer-milled then combined with the other components and the slurry ground in a sand mill until substantially all particles are smaller than 5 microns.

This formulation is mixed with water at the rate of 2 kilograms of active ingredient per 400 liters of water and 2 kilograms of polyoxyethylene sorbitan monolaurate are added. This suspension is sprayed to run-off on roadside vegetation containing a mixture of grasses and herbaceous annuals and perennials.

The treatment retards the growth of vegetation along the roadside and reduces the number of mowings necessary to maintain a neat road right-of-way. The treatment also prevents the flowering and seed set on many of the plants present, thereby reducing the seed present to propagate undesirable annual weedy grasses and broad-leaves.

EXAMPLE 4

|  | Percent |
|---|---|
| 3-(2-carboxyphenyl)-5-(4-chlorophenyl)-pyrazole | 5.00 |
| Fine silica | 1.25 |
| Granular vermiculite | 88.75 |
| Trimethylnonyl polyethylene glycol ether | 5.00 |

The active component and fine silica are first blended and hammer-milled, then blended gently with the granular vermiculite. The surfactant is mixed with an equal weight of water and sprayed upon the mixture previously prepared. The water is permitted to evaporate to give the final product.

Using a conventional granular application, the above formulation is spread over freshly cultivated, weed-free peanuts at the rate of 20 kilograms per hectare. The granules effectively penetrate the peanut foliage. Annual broadleaf weeds are prevented from growing while the crop is not injured and yields are good.

EXAMPLE 5

One kilogram of the formulation of Example 3 and two kilograms of maleic hydrazide are dispersed in 400 liters of water. This mixture is applied to run-off as a foliar spray to trimmed trees with about four inches of regrowth, along a power line right-of-way.

This curtails growth of the trimmed trees. The trees require less frequent trimming to keep them below the transmission lines.

EXAMPLE 6

|  | Percent |
|---|---|
| 3-(2-carbomethoxyphenyl)-5-(4-methoxyphenyl)-pyrazole | 80.0 |
| Alkylnaphthalenesulfonic acid, Na salt | 1.5 |
| Partially desulfonated sodium lignin sulfonate | 2.0 |
| Synthetic fine silica | 16.5 |

The above components are mixed in a ribbon blendor, hammer-milled until substantially all particles are smaller than fifty microns and reblended to yield a readily dispersible wettable powder for application as an aqueous spray.

Three kilograms of such formulation is suspended in 500 liters of water and one kilogram of nonphytotoxic wetting agent such as polyoxyethylene sorbitan monolaurate is added.

The resulting suspension is sprayed over the top of a hectare of sugar cane about forty days prior to harvest.

The treated plants do not flower before harvest while sugar cane in an adjacent untreated field develops flowers. The treated plants yield increased amounts of sugar.

EXAMPLE 7

A cotton field is sprayed about two-thirds of the way through the normal growing season with 3-(2-carbomethoxyphenyl)-5-(4-methoxyphenyl)pyrazole at the rate of one kilogram active per hectare in the formulation of Example 1. The sprayed cotton plants stop growing and set no new bolls. The bolls already present, however, develop especially well and produce an early yield of high-quality lint. Also, due to the smaller amount of foliage and lack of developing bolls, insect control is better and fewer insects survive the winter to infest next year's crop.

EXAMPLE 8

The following formulation is prepared:

|  | Percent |
|---|---|
| 3-(2-carboxyphenyl)-5-phenylpyrazole | 80 |
| bentonite (Wyoming) | 15 |
| sodium ligninsulfonate | 3 |
| sodium alkylnaphthalenesulfonate | 2 |

The ingredients are blended thoroughly and passed through a hammer mill to produce a wettable powder with less than 10% of the product coarser than 50 microns.

A peanut field is treated at cracking with the above formulation at the rate of one kilogram active ingredient per hectare. A heavy population of mixed annual weeds is controlled without injury to the peanuts.

EXAMPLE 9

A mixture of 4.3 parts of ethanolamine, 25 parts of 2-butoxyethanol and 52.1 parts of water was stirred and maintained at about room temperature while adding 18.6 parts of 3-(2-carboxyphenyl)-5-phenylpyrazole in portions. The resulting solution contains 1.5 lbs per gallon of the ethanolamine salt of 3-(2-carboxyphenyl)-5-phenylpyrazole.

One kilogram of active ingredient formulated as described above is dissolved in 300 liters of water and applied to a hectare of peanuts infested with Florida beggarweed (*Desmodium tortosum*), cocklebur (Xanthium spp.) and sicklepod (*Cassia obtusifolia*). The peanuts are in the sixth true leaf stage. The treatment controls the weeds and the peanuts recover from temporary hormonal symptoms and grow well, providing a good yield.

EXAMPLE 10

One kilogram per hectare of 3-(2-carbomethoxyphenyl)-5-(4-chlorophenyl)pyrazole formulated as in Example 1 is applied to a field in which cabbage plants have just been set. The treatment prevents the growth of annular weeds whereas the cabbage grows well.

EXAMPLE 11

A soybean field containing such troublesome broad-leaved weeds as cocklebur, *Xanthium pensylvanicum;* morningglory, Impomoed Spp.; bindweed, *Convolvulus arvensis;* sicklepod, *Cassia obtusifolia;* and teaweed; *Sida spinosa,* is sprayed with 3-(2-carbomethoxyphenyl)-5-(4-chlorophenyl)pyrazole formulated as in Example 1 at the rate of three-fourths of a kilogram active per hectare. The application is made before the weeds blossom and it is directed in such a way that the foliage of the weeds is wetted but that the soybean plants are largely missed. The weeds are killed or severely stunted. Those that survive produce no viable seed. The soybeans, on the other hand, grow well and produce a large yield.

EXAMPLE 12

A dense stand of soybeans at the one-tenth to full blossom stage is sprayed with a foliar application of 3-(2-carboxyphenyl)-5-phenylpyrazole at the rate of 12 grams active ingredient per hectare formulated as in Example 8. Apical dominance is eliminated, the stem is enlarged, and the lateral branches are released permitting a greater number of new flowers to develop and set a larger number of pods per plant. The controlled vegative growth makes the plant extremely resistant to lodging and the plants remain upright under severe weather conditions while untreated plants are lodged. The total yield is increased over similar untreated areas (control) and the upright plants facilitate harvest over the lodged controls.

|  | Rate lb/A | Yield bu/A | % of Control |
|---|---|---|---|
| Control | — | 42.7 | 100 |
| 3-(2-carboxyphenyl)-5-phenyl-pyrazole | 0.004 | 51.2 | 120 |

EXAMPLE 13

|  | Percent |
|---|---|
| 3-(2-carboxyphenyl)-5-(4-fluorophenyl)-pyrazole | 25 |
| polyoxyethylene sorbitol hexaoleate | 5 |
| highly aliphatic hydrocarbon oil | 70 |

The ingredients are ground together in a sand mill until the solid particles have been reduced to less than about 5 microns. The resulting thick suspension may be applied directly, extended with oils, or emulsified in water.

Peanuts at the pegging stage are sprayed with one-fourth kilogram active ingredient per hectare of the above formulation. Strength of shell and vine attachment is increased and greater yields are recovered than where no treatment is applied.

EXAMPLE 14

|  | Percent |
|---|---|
| 3-(2-carboxyphenyl)-5-(p-tolyl)pyrazole | 1 |
| isophorone | 94 |
| blend of oil-soluble sulfonates and polyoxyethylene ethers | 5 |

The ingredients are combined and stirred to yield a solution. A fine screen filter is included in the packaging line to insure the absence of any undissolved matter in the final product.

A planting of gynecious hybrid pickling cucumbers is sprayed just before flowering with the above material. Five hundred liters of water per hectare containing 50 parts per million active ingredient is applied. Parthenocarpic fruit develop and yields are increased.

EXAMPLE 15

|  | Percent |
|---|---|
| 3-(2-carboxyphenyl)-5-(3-pyridyl)pyrazole | 50.0 |
| polyacrylic acid thickener | 0.3 |
| dodecylphenyl polyethyleneglycol ether | 0.5 |
| polyvinyl alcohol | 1.0 |
| pentachlorophenol | 0.4 |
| water | 47.8 |

The ingredients are ground together in a sand mill to produce particles substantially all under 5 microns in size.

A rape planting severely infested with cleavers (Galium spp.) is sprayed with one kilogram per hectare of the formulation before the cleavers form flowers. Spraying is done by aircraft using 100 liters of water per hectare as carrier. The weed is controlled and rape seed yields are improved.

EXAMPLE 16

|  | Percent |
|---|---|
| 3-(2-carboxyphenyl)-5-(2-furyl)pyrazole | 2.5 |
| dimethylformamide | 97.5 |

The ingredients are combined and stirred with warming to produce a solution. This can be used for low-volume applications.

The formulation is sprayed by aircraft at the rate of 5 liters per hectare over soybeans at the initial fruit set stage. Vegetative growth is terminated but pod development continues. Lodging is reduced and harvested yield increased.

Chemical Preparation Examples

EXAMPLE 17

3-(2-Carboxyphenyl)-5-phenylpyrazole

To a stirred solution of 60 g of acetophenone in 300 ml of dimethylformamide is added 24 g of a 50% sodium hydride-mineral oil slurry. This mixture is stirred without heating for 3 hours, or until hydrogen evolution ceases.

To a solution of 74 g of phthalic anhydride in 300 ml of dimethylformamide is added 26 g of sodium methoxide. After one-half hour this mixture is introduced into the sodio-acetophenone solution. The resulting mixture is stirred at 120° for three hours; the crystals are filtered, washed with acetone, and dried to yield 118 g of the disodium salt of 2-benzoylacetylbenzoic acid.

To a slurry of 100 g of the disodium salt of 2-benzoylacetylbenzoic acid in 400 ml of methanol is added first 12.5 g concentrated hydrochloric acid, followed by 11 g of hydrazine hydrate. This reaction mixture is heated at reflux for ½ hour, cooled to 5°–10°, acidified to pH 3 with concentrated hydrochloric acid, and diluted with 300 ml of water. The crystals are filtered off and recrystallized from ethanol-water, yielding 59 g of 3-(2-carboxyphenyl)-5-phenylpyrazole, mp 204°–205.5°.

By the procedure of Example 17, using the anhydrides and ketones shown, the following pyrazoles are prepared.

| Ex. No. | Anhydride | Ketone | Product | Melting Point |
|---|---|---|---|---|
| 18 | phthalic anhydride | 3-methoxyacetophenone | 3-(2-carboxyphenyl)-5-(3-methoxyphenyl)pyrazole | 170–172° |
| 19 | phthalic anhydride | methyl t-butyl ketone | 3-(2-carboxyphenyl)-5-t-butylpyrazole | 164.5–166.5° |
| 20 | phthalic anhydride | 4-fluoroacetophenone | 3-(2-carboxyphenyl)-5-(4-fluorophenyl)pyrazole | 252–254° |
| 21 | phthalic anhydride | 4-methylacetophenone | 3-(2-carboxyphenyl)-5-(4-methylphenyl)pyrazole | 222–225° |
| 22 | phthalic anhydride | 3-acetylpyridine | 3-(2-carboxyphenyl)-5-(3-pyridyl)pyrazole | |
| 23 | 4-methylphthalic anhydride | acetophenone | 3-(2-carboxy-4-methylphenyl)-5-phenylpyrazole | 182–185° |
| 24 | phthalic anhydride | 3-bromoacetophenone | 3-(2-carboxyphenyl)-5-(3-bromophenyl)pyrazole | 232–236° |
| 25 | phthalic anhydride | 2,4,6-trimethylacetophenone | 3-(2-carboxyphenyl)-5-(2,4,6-trimethylphenyl)pyrazole | 190–194° |
| 26 | phthalic anhydride | 4-chloroacetophenone | 3-(2-carboxyphenyl)-5-(4-chlorophenyl)pyrazole | 258.5–260° |
| 27 | phthalic anhydride | 2-methoxyacetophenone | 3-(2-carboxyphenyl)-5-(2-methoxyphenyl)pyrazole | 251–251.5° |
| 28 | 4-fluorophthalic anhydride | acetophenone | 3-(2-carboxy-4-fluorophenyl)-5-phenylpyrazole | |
| 29 | 4-bromophthalic anhydride | acetophenone | 3-(2-carboxy-4-bromophenyl)-5-phenylpyrazole | |
| 30 | phthalic anhydride | 3,4-dichloroacetophenone | 3-(2-carboxyphenyl)-5-(3,4-dichlorophenyl)pyrazole | |
| 31 | phthalic anhydride | 2,5-dibromoacetophenone | 3-(2-carboxyphenyl)-5-(2,5-dibromophenyl)pyrazole | |
| 32 | phthalic anhydride | 2,5-dimethoxyacetophenone | 3-(2-carboxyphenyl)-5-(2,5-dimethoxyphenyl)pyrazole | |
| 33 | phthalic anhydride | 3-methyl-5-ethylacetophenone | 3-(2-carboxyphenyl)-5-(3-methyl-5-ethylphenyl)pyrazole | |
| 34 | phthalic anhydride | 3,4,5-trichloroacetophenone | 3-(2-carboxyphenyl)-5-(3,4,5-trichlorophenyl)pyrazole | |
| 35 | 4-chlorophthalic anhydride | acetophenone | 3-(2-carboxy-5-chlorophenyl)-5-phenylpyrazole | |
| 36 | phthalic anhydride | 2-butylsulfonylacetophenone | 3-(2-carboxyphenyl)-5-(2-butylsulfonylphenyl)pyrazole | |
| 37 | phthalic anhydride | 3-trifluoromethylacetophenone | 3-(2-carboxyphenyl)-5-(3-trifluoromethylphenyl)pyrazole | |
| 38 | phthalic anhydride | 3-acetylindole | 3-(2-carboxyphenyl)-5-(3-indolyl)pyrazole | |
| 39 | phthalic anhydride | 3-(n-butylthio)acetophenone | 3-(2-carboxyphenyl)-5-(3-n-butylthiophenyl)pyrazole | |
| 40 | phthalic anhydride | 4-iodoacetophenone | 3-(2-carboxyphenyl)-5-(4-iodophenyl)pyrazole | |
| 41 | phthalic anhydride | 4-butylacetophenone | 3-(2-carboxyphenyl)-5-(4-butylphenyl)pyrazole | |
| 42 | phthalic anhydride | 3-isopropylacetophenone | 3-(2-carboxyphenyl)-5-(3-isopropylphenyl)pyrazole | |
| 43 | phthalic anhydride | 4-t-butyloxyacetophenone | 3-(2-caboxyphenyl)-5-(4-t-butyloxyphenyl)pyrazole | |
| 44 | phthalic anhydride | 3-(methylthio)acetophenone | 3-(2-carboxyphenyl)-5-(3-methylthiophenyl)pyrazole | |
| 45 | phthalic anhydride | 4-methylsulfonylacetophenone | 3-(2-carboxyphenyl)-5-(4-methylsulfonylphenyl)pyrazole | |

EXAMPLE 46

2-(4-Methoxyphenyl)pyrazolo[5,1-a]isoindol-8-one

A mixture of 62.00 g 2-(4-methoxyphenyl)-3,3a-dihydro-8-H-pyrazolo[5,1-a]isoindol-8-one, 1100 ml of benzene, and 27.2 g. of 2,3-dichloro-5,6-dicyanobenzoquinone was heated under reflux for 2 hours under nitrogen atmosphere. A further 27.2 g of 2,3-dichloro-5,6-dicyanobenzoquinone was added, and the heating was continued for a total of 8 hours. After cooling to 25°, the solid residue was filtered off, and the filtrate was evaporated to dryness under vacuum. The combined solids from the filter and evaporation flask were stirred mechanically for 1 hour with a mixture of 20 g of 85% potassium hydroxide and 1500 g of water. The mixture was filtered, the yellow solid was washed successively with 2 × 500-ml of 5% sodium bicarbonate, 2 × 500-ml of water, and air-dried. The yellow residue was recrystallized from 3000 ml of acetone to yield 55 g (80%) of 2-(4-methoxyphenyl)pyrazolo[5,1-a]isoindol-8-one, mp 180°–181°.

EXAMPLE 47

3-(2-Carbomethoxyphenyl)-5-(4-methoxyphenyl)-pyrazole and its hydrochloride.

A mixture of 2-(4-methoxyphenyl)pyrazolo[5,1-a]isoindol-8-one (100 mg), methanol (10 ml), and sodium (0.1 g). was stirred overnight at 25°. Evaporation of the methanol left 120 mg (96%) of colorless gum which was the ester 3-(2-carbomethoxyphenyl)-5-(4-methoxyphenyl)pyrazole. The crude ester was dissolved in benzene and stirred overnight with 2 g of Florisil. Filtration and evaporation of the benzene solution, followed by recrystallization from hexane-ethyl acetate (1:1), gave 3-(2-carbomethoxyphenyl)-5-(4-methoxyphenyl)pyrazole, mp 92–93°.

The ester, 3-(2-carbomethoxyphenyl)-5-(4-methoxyphenyl)pyrazole, was dissolved in ether, cooled to 0° and the solution was saturated with gaseous hydrogen chloride. The resulting colorless precipitate of 3-(2-carbomethoxyphenyl)-5-(4-methoxyphenyl)pyrazole hydrochloride was filtered off, rinsed with ether and dried by suction, yield 105 mg (85%). The crude hydrochloride of 3-(2-carbomethoxyphenyl)-5-(4-methoxyphenyl)pyrazole was recrystallized from acetone (10 ml), recovery 43.9 mg after drying at 25° (0.1 mm). The product had mp 187°–189°.

Anal. Calcd. for $C_{18}H_{17}N_2O_3Cl$: C, 62.70; H, 4.97; N, 8.13; Found: C, 62.71; H, 4.86; N, 7.99.

By substitution of 100% phosphoric, sulfuric, or nitric acid for hydrogen chloride of Example 51, the following salts are generated:

| Ex. | |
|---|---|
| 52. | 3-(2-carbomethoxyphenyl)-5-(4-methoxyphenyl)pyrazole, phosphoric acid salt |

-continued

| Ex. | |
|---|---|
| 53. | 3-(2-carbomethoxyphenyl)-5-(4-methoxyphenyl)pyrazole, sulfuric acid salt, and |
| 54. | 3-(2-carbomethoxyphenyl)-5-(4-methoxyphenyl)pyrazole, nitric acid salt |

EXAMPLE 48

3-(2-Carboethoxyphenyl)-5-(4-methoxyphenyl)-pyrazole

A mixture of 2-(4-methoxyphenyl)pyrazole[5,1-a]isoindol-8-one (100 mg) and ethanol (20 ml) was stirred overnight at 25°. The dissolution was slow, so a chip of sodium metal was added, which caused an almost immediate reaction, judged by the disappearance of the yellow color 3-(2-carboethoxyphenyl)-5-(4-methoxyphenyl)pyrazole. The solvent was evaporated to leave the colorless gummy 3-(2-carboethoxyphenyl)-5-(4-methoxyphenyl)pyrazole, which was recrystallized from hexane-ethyl acetate, and exhibited mp 99.5°–101°.

Using the procedure of Example 48, and the starting material and reactant indicated below, the following pyrazoles are prepared:

| Ex. No. | Starting Material | Reactant | Product | Melting Point |
|---|---|---|---|---|
| 49 | 2-(4-methyoxyphenyl)-8H-pyrazolo-[5,1-a]isoindol-8-one | $CH_3CH_3CH_2OH$ | 3-(2-carbopropoxyphenyl)-5-(4-methoxyphenyl)pyrazole | 107–109° |
| 50 | 2-(4-methoxyphenyl)-8H-pyrazolo-[5,1-a]isoindol-8-one | $CH_3CH_2CH_2CH_2OH$ | 3-(2-carbobutoxyphenyl)-5-(4-methoxyphenyl)pyrazole | 92–94° |
| 51 | 2-(4-methoxyphenyl)-8H-pyrazolo-[5,1-a]isoindol-8-one | $CH_3CH_2CH_2CH_2CH_2OH$ | 3-(2-carbopentoxyphenyl)-5-(4-methoxyphenyl)pyrazole | 82–83.5° |
| 52 | 2-(3-nitrophenyl)-5-methyl-8H-pyrazolo[5,1-a]isoindol-8-one | $(CH_3)_2CH-OH$ | 3-(2-carboisopropoxy-5-methyl-phenyl)-5-(3-nitrophenyl)-pyrazole | |
| 53 | 2-phenyl-8H-pyrazolo[5,1-a]-isoindol-8-one | $HO-CH_2-CH_2OH$ | 3-[2-(2-hydroxyethoxycarbonyl)-phenyl]-5-phenylpyrazole | 94–95.5° |
| 54 | 2-phenyl-8H-pyrazolo[5,1-a]-isoindol-8-one | $(CH_3)_2CH-OH$ | 3-(2-carboisopropoxyphenyl)-5-phenylpyrazole | |
| 55 | 2-phenyl-8H-pyrazolo[5,1-a]-isoindol-8-one | $CH_3OH$ | 3-(2-carbomethoxyphenyl)-5-phenylpyrazole | 103.5–105° |
| 56 | 2-phenyl-8H-pyrazolo[5,1-a]-isoindol-8-one | $CH_3CH_2CH_2OH$ | 3-(2-carbopropoxyphenyl)-5-phenylpyrazole | 64–67° |
| 57 | 2-phenyl-8H-pyrazolo[5,1-a]-isoindol-8-one | $C_6H_5CH_2OH$ | 3-(2-carbobenzyloxyphenyl)-5-phenylpyrazole | |
| 58 | 2-phenyl-8H-pyrazolo[5,1-a]-isoindol-8-one | $CH_3OCH_2CH_2OH$ | 3-[2-(2-methoxyethoxycarbonyl)-phenyl]-5-phenylpyrazole | |
| 59 | 2-phenyl-8H-pyrazolo[5,1-a]-isoindol-8-one | $CH_3CH_2CH_2OCH_2CH_2OH$ | 3-[2-(2-propoxyethoxycarbonyl)-phenyl]-5-phenylpyrazole | |

EXAMPLE 60

3-(2-Carboxyphenyl)-5-(4-methoxyphenyl)pyrazole

A mixture of 2-(4-methoxyphenyl)-8H-pyrazolo[5,1-a]isoindol-8-one (100 mg), water (5 ml) and methanol (5ml) was stirred for one hour with sodium hydroxide (0.5 g). Within 5 minutes, a colorless solution has been produced. The mixture was then acidified to pH 3 with concentrated hydrochloric acid, cooled to 0° and filtered. The colorless crystalline residue was rinsed with water and air-dried. It was recrystallized from 33% aqueous ethanol (15 ml), recovery 80.7 mg (79%) of colorless crystals, mp 223°–225° dec, of 3-(2-carboxyphenyl)-5-(4-methoxyphenyl)pyrazole.

Anal. Calcd. for $C_{17}H_{14}N_2O_3$: C, 69.37; H, 4.80; N, 9.52; Found: C, 69.19; H, 4.68; N, 9.43.

Using the procedure of Example 60, and the starting material indicated below, the following pyrazoles are prepared:

| Ex. No. | Starting Material | Product | Melting Point |
|---|---|---|---|
| 61 | 5,6-dihydro-3-methoxy-11H-naphth-[1', 2':3,4]pyrazolo[5,1-a]isoindol- | 2-(4,5-dihydro-7-methoxy-2H-benz-[g]indazol-3-yl)benzoic acid | 228–230° |
| 62 | 3-methoxy-11H-naphth[1', 2':3,4]pyrazolo[5,1-a]isoindol-11-one | 2-(7-methoxy-2H-benz[g]indazol-3-yl)benzoic acid | 270–274° |
| 63 | 2-(2-thienyl)-8H-pyrazolo[5,1-a]isoindol-8-one | 3-(2-carboxyphenyl)-5-(2-thienyl)pyrazole | |
| 64 | 2-(2-furyl)-8H-pyrazolo[5,1-a]isoindol-8-one | 3-(2-carboxyphenyl)-5-(2-furyl)pyrazole | |
| 65 | 2-(4-nitrophenyl)-8H-pyrazolo[5,1-a]isoindol-8-one | 3-(2-carboxyphenyl)-5-(4-nitrophenyl)pyrazole | |
| 66 | 2-isopropyl-8H-pyrazolo[5,1-a]isoindol-8-one | 3-(2-carboxyphenyl)-5-isopropylpyrazole | |
| 67 | 2-(1-ethylpropyl)-8H-pyrazolo[5,1-a]isoindol-8-one | 3-(2-carboxyphenyl)-5-(1-ethylpropyl)pyrazole | |
| 68 | 2-(1,1-dimethylpropyl)-8H-pyrazolo[5,1-a]isoindol-8-one | 3-(2-carboxyphenyl)-5-(1,1-dimethylpropyl)pyrazole | |
| 69 | 2-cyclopentyl-8H-pyrazolo[5,1-a]isoindol-8-one | 3-(2-carboxyphenyl)-5-cyclopentylpyrazole | |
| 70 | 2-biphenyl-8H-pyrazolo[5,1-a]isoindol-8-one | 3-(2-carboxyphenyl)-5-biphenylpyrazole | 249–251.5° |

EXAMPLE 71

3-(2-Carboxyphenyl)-5-phenylpyrazole was dissolved in hot water, treated with sodium hydroxide solution, and cooled to 5° to give a precipitate of 3-(2-carboxyphenyl)-5-phenylpyrazole, sodium salt.

By the procedure of Example 71, using 3-(2-carboxyphenyl)-5-phenylpyrazole and the indicated reactant, the following salts are prepared.

| Ex. No. | Reactant | Product |
|---|---|---|
| 72 | LiOH | 3-(2-carboxyphenyl)-5-phenylpyrazole, lithium salt |
| 73 | KOH | 3-(2-carboxyphenyl)-5-phenylpyrazole, potassium salt |
| 74 | Ca(OH)$_2$ | 3-(2-carboxyphenyl)-5-phenylpyrazole, calcium salt |
| 75 | Mg(OH)$_2$ | 3-(2-carboxyphenyl)-5-phenylpyrazole, magnesium salt |
| 76 | (CH$_3$)$_4$N$^+$OH$^-$ | 3-(2-carboxyphenyl)-5-phenylpyrazole, tetramethylammonium salt |
| 77 | (CH$_3$)$_3$N, H$_2$O | 3-(2-carboxyphenyl)-5-phenylpyrazole, trimethylammonium salt |
| 78 | (CH$_3$)$_2$NH, H$_2$O | 3-(2-carboxyphenyl)-5-phenylpyrazole, dimethylammonium salt |
| 79 | CH$_3$NH$_2$, H$_2$O | 3-(2-carboxyphenyl)-5-phenylpyrazole, methylammonium salt |
| 80 | C$_{12}$H$_{25}$NH$_2$, H$_2$O | 3-(2-carboxyphenyl)-5-phenylpyrazole, dodecylammonium salt |
| 81 | C$_6$H$_5$CH$_2$NH$_2$, H$_2$O | 3-(2-carboxyphenyl)-5-phenylpyrazole, benzylammonium salt |
| 82 | HOCH$_2$CH$_2$NH$_2$, H$_2$O | 3-(2-carboxyphenyl)-5-phenylpyrazole, β-hydroxyethylammonium salt |
| 83 | HOCH$_2$CH$_2$CH$_2$CH$_2$NH$_2$, H$_2$O | 3-(2-carboxyphenyl)-5-phenylpyrazole, 4-hydroxybutylammonium salt |
| 84 | C$_4$H$_9$NH$_2$, H$_2$O | 3-(2-carboxyphenyl)-5-phenylpyrazole, n-butylammonium salt |

EXAMPLE 85

A mixture of 2-(4-methoxyphenyl)-8H-pyrazolo[5,1-a]isoindol-8-one and excess concentrated hydriodic acid was heated at reflux for 6 hours and poured onto ice; the crude solid was recrystallized from ethanol:dimethyl sulfoxide:water (3:1:1) to give 5-(4-hydroxyphenyl)-3-(2-carboxyphenyl)pyrazole, m.p. 260°–264°.

EXAMPLE 86

A mixture of 30 g 3-(2-carbomethoxyphenyl)-5-(4-methoxyphenyl)pyrazole, 0.30 g sodium hydride and 0.8 g acetyl chloride in 50 ml anhydrous tetrahydrofuran (THF) is stirred and refluxed overnight. The reaction mixture is filtered and the THF is removed from the filtrate to yield 1-acetyl-3-(2-carbomethoxyphenyl)-5-(4-methoxyphenyl)-pyrazole.

EXAMPLE 87

A mixture of 100 ml of dimethylformamide, 13.0 g of 3-(2-carboxyphenyl)-5-(4-methoxyphenyl)pyrazole, 9.36 g of sodium carbonate, and 25 ml of methyl iodide was heated at reflux for 6 hours, then poured into 500 ml of water, acidified to pH 3, and extracted with chloroform. The yellow oil obtained from the extracts was chromatographed on 100 g of Silicar CC-4, taking 200-ml fractions. Fractions 1–6 (2:1 cyclohexane:ethyl acetate) contained 6.04 g of 1-methyl-3-(2-carbomethoxyphenyl)-5-(4-methoxyphenyl)-pyrazole.

EXAMPLE 88

Treatment of the disodium salt of 2-benzoylacetylbenzoic acid with methylhydrazine, as in Example 17, followed by recrystallization of the product from ethanol-water, yields 1-methyl-3-(2-carboxyphenyl)-5-phenylpyrazole, mp 163°–165° (dec.).

Using the procedure of Example 88, the following pyrazoles can be prepared.

| Ex. No. | Starting Material | Reactant | Product |
|---|---|---|---|
| 89 | 2-benzoylacetylbenzoic acid, disodium salt | (CH$_3$)$_2$CH—NHNH$_2$ | 1-isopropyl-3-(2-carboxyphenyl)-5-phenylpyrazole |
| 90 | 2-benzoylacetylbenzoic acid, disodium salt | CH$_3$(CH$_2$)$_3$—NHNH$_2$ | 1-butyl-3-(2-carboxyphenyl)-5-phenylpyrazole |

EXAMPLE 91

A mixture of 5.0 g of 5-(4-methoxyphenyl)-3-(2-carbomethoxyphenyl)pyrazole, 3.5 g of acetic anhydride, and 25 ml of pyridine was allowed to stir overnight at 25°. The mixture was poured into 100 ml of ice water, and the product was extracted with benzene. Recrystallization from hexane-ethyl acetate (2:1) gave 1-acetyl-3-(2-carbomethoxyphenyl)-5-(4-methoxyphenyl)-pyrazole, mp 119°–121°.

By the procedure of Example 91, using 3-(2-carbomethoxyphenyl)-5-(4-methoxyphenyl)pyrazole and the indicated reactant, the following pyrazoles can be prepared.

| Ex. No. | Reactant | Product | Melting Point |
|---|---|---|---|
| 92 | butyric anhydride | 1-butyryl-3-(2-carbomethoxyphenyl)-5-(4-methoxyphenyl)-pyrazole | 65–69° |
| 93 | propionic anhydride | 1-proionyl-3-(2-carbomethoxyphenyl)-5-(4-methoxyphenyl)-pyrazole | 71–73.5° |
| 94 | methyl chloroformate | 1-carbomethoxy-3-(2-carbomethoxyphenyl)-5-(4-methoxyphenyl)pyrazole | |
| 95 | butyl chloroformate | 1-carbobutoxy-3-(2-carbomethoxyphenyl)-5-(4-methoxyphenyl)pyrazole | |
| 96 | benzenesulfonyl chloride | 1-benzenesulfonyl-3-(2-carbomethoxyphenyl)-5-(4-methoxyphenyl)pyrazole | |
| 97 | 4-methylphenylsulfonyl chloride | 1-(4-methylphenylsulfonyl)-3-(2-carbomethoxyphenyl)-5-(4-methoxyphenyl)pyrazole | |
| 98 | p-chlorophenylsulfonyl chloride | 1-(4-chlorophenylsulfonyl)-3-(2-carbomethoxyphenyl)-5-(4-methoxyphenyl)pyrazole | |

EXAMPLE 99

A mixture of 3-(2-carboxy-1-cyclohexen-1-yl)-5-phenylpyrazole (15.0 g) and pyridine (125 ml) is treated at 25° C with thionyl chloride (13.5 g); after stirring for 2 hours, ethanol (40.0 g) is added, and the mixture is stirred for 3 hours. The reaction mixture is partitioned between water and methylene chloride; the organic layer is washed with water and evaporated to give 3-(2-carboethoxy-1-cyclohexen-1yl)-5-phenylpyrazole.

By the procedure of Example 99, using the reaction product of thionyl chloride with 3-(2-carboxy-1-cyclohexen-1-yl)-5-phenylpyrazole and the reactants indicated below, the following pyrazoles are prepared.

| Ex. No. | Reactant | Product |
|---|---|---|
| 100 | C<sub>6</sub>H<sub>5</sub>CH<sub>2</sub>OH | 3-(2-carbobenzyloxy-1-cyclohexen-1-yl)-5-phenylpyrazole |
| 101 | CH<sub>3</sub>OH | 3-(2-carbomethoxy-1-cyclohexen-1-yl)-5-phenylpyrazole |
| 102 | (CH<sub>3</sub>)<sub>2</sub>CHOH | 3-(2-carboisopropoxy-1-cyclohexen-1-yl)-5-phenylpyrazole |
| 103 | CH<sub>3</sub>.(CH<sub>2</sub>)<sub>5</sub>.OH | 3-(2-carbohexyloxy-1-cyclohexen-1-yl)-5-phenylpyrazole |
| 104 | HOCH<sub>2</sub>CH<sub>2</sub>OH | 3-[2-(2-hydroxyethoxycarbonyl)-1-cyclohexen-1-yl]-5-phenylpyrazole |
| 105 | HOCH<sub>2</sub>CH<sub>2</sub>CH<sub>2</sub>OH | 3-[2-(3-hydroxypropoxycarbonyl)-1-cyclohexen-1-yl]-5-phenylpyrazole |

EXAMPLE 106

3-(2-Carboxy-1-cyclohexen-1-yl)-5-phenylpyrazole

A mixture of 24.0 g of acetophenone, 19.2 g of a 50% sodium hydride-mineral oil slurry, and 170 ml of dimethylformamide is stirred for 2 hours, or until hydrogen evolution ceases.

To a solution of 30.4 g of 3,4,5,6-tetrahydrophthalic anhydride in 150 ml of dimethylformamide is added 11.0 g of sodium methoxide. After ½ hour this mixture is introduced into the sodio-acetophenone solution. The resulting mixture is stirred at 120° for 3 hours; the solid precipitate is filtered off, washed with acetone and ether, and dried to yield the crude disodium salt of 2-benzoylacetyl-1-cyclohexenecarboxylic acid.

To a slurry of 31.6 g of the disodium salt of 2-benzoylacetyl-1-cyclohexenecarboxylic acid in 150 ml of methanol is added 12 g of concentrated hydrochloric acid, followed by 12 g of hydrazine hydrate. The reaction mixture is refluxed for 2 hours, cooled to 5°, acidified to pH 3, and diluted with 150 ml of water. The solid is collected and recrystallized from acetic acid-water to give 11.4 g of 3-(2-carboxy-1-cyclohexen-1-yl)-5-phenylpyrazole, m.p. 207–209°.

By the procedure of Example 106, using 3,4,5,6-tetrahydrophthalic anhydride and the ketones shown, the following pyrazoles are prepared.

| Ex. No. | Ketone | Product |
|---|---|---|
| 107 | methyl cyclohexyl ketone | 3-(2-carboxy-1-cyclohexen-1-yl)-5-cyclohexylpyrazole |
| 108 | 1-acetylnaphthalene | 3-(2-carboxy-1-cyclohexen-1-yl)-5-(1-naphthyl)pyrazole |
| 109 | 2-acetylnaphthalene | 3-(2-carboxy-1-cyclohexen-1-yl)-5-(2-naphthyl)pyrazole |
| 110 | 2-acetylfuran | 3-(2-carboxy-1-cyclohexen-1-yl)-5-(2-furyl)pyrazole |
| 111 | 2-acetylthiophene | 3-(2-carboxy-1-cyclohexen-1-yl)-5-(2-thienyl)pyrazole |
| 112 | 2-acetylpyridine | 3-(2-carboxy-1-cyclohexen-1-yl)-5-(2-pyridyl)pyrazole |
| 113 | 4-acetylpyridine | 3-(2-carboxy-1-cyclohexen-1-yl)-5-(4-pyridyl)pyrazole |
| 114 | 3-acetylindole | 3-(2-carboxy-1-cyclohexen-1-yl)-5-(3-indolyl)pyrazole |
| 115 | 1-indanone | 2-(2,4-dihydroindeno[1,2-c]pyrazol-3-yl)-1-cyclohexene-1-carboxylic acid |
| 116 | α-tetralone | 2-(4,5-dihydro-2H-benz[g]indazol-3-yl)-1-cyclohexene-1-carboxylic acid |
| 117 | 3-bromoacetophenone | 3-(2-carboxy-1-cyclohexen-1-yl)-5-(3-bromophenyl)pyrazole |
| 118 | 2-fluoroacetophenone | 3-(2-carboxy-1-cyclohexen-1-yl)-5-(2-fluorophenyl)pyrazole |
| 119 | 4-methylacetophenone | 3-(2-carboxy-1-cyclohexen-1-yl)-5-(4-methylphenyl)pyrazole |
| 120 | 3-butylacetophenone | 3-(2-carboxy-1-cyclohexen-1-yl)-5-(3-butylphenyl)pyrazole |
| 121 | 4-hydroxyacetophenone | 3-(2-carboxy-1-cylohexen-1-yl)-5-(4-hydroxyphenyl)pyrazole |
| 122 | 3-methoxyacetophenone | 3-(2-carboxy-1-cyclohexen-1-yl)-5-(3-methoxyphenyl)pyrazole |
| 123 | 4-butoxyacetophenone | 3-(2-carboxy-1-cyclohexen-1-yl)-5-(4-butoxyphenyl)pyrazole |

-continued

| Ex. No. | Ketone | Product |
|---|---|---|
| 124 | 2-(methylthio)acetophenone | 3-(2-carboxy-1-cyclohexen-1-yl)-5-[2-(methylthio)phenyl]-pyrazole |
| 125 | 4-(butylthio)acetophenone | 3-(2-carboxy-1-cyclohexen-1-yl)-5-[4-(butylthio)phenyl]-pyrazole |
| 126 | 3-nitroacetophenone | 3-(2-carboxy-1-cyclohexen-1-yl)-5-(3-nitrophenyl)pyrazole |
| 127 | 4-methylsulfonylacetophenone | 3-(2-carboxy-1-cyclohexen-1-yl)-5-(4-methylsulfonylphenyl)-pyrazole |
| 128 | 2-(trifluoromethyl)acetophenone | 3-(2-carboxy-1-cyclohexen-1-yl)-5-[2-(trifluoromethyl)phenyl]-pyrazole |
| 129 | 3,4-dichloroacetophenone | 3-(2-carboxy-1-cyclohexen-1-yl)-5-(3,4-dichlorophenyl)-pyrazole |
| 130 | 2,5-dimethoxyacetophenone | 3-(2-carboxy-1-cyclohexen-1-yl)-5-(2,5-dimethoxyphenyl)-pyrazole |
| 131 | 3,5-dimethylacetophenone | 3-(2-carboxy-1-cyclohexen-1-yl)-5-(3,5-dimethylphenyl)-pyrazole |
| 132 | 3,4,5-trichloroacetophenone | 3-(2-carboxy-1-cyclohexen-1-yl)-5-(3,4,5-trichlorophenyl)-pyrazole |
| 133 | 3,4,5-trimethylacetophenone | 3-(2-carboxy-1-cyclohexen-1-yl)-5-(3,4,5-trimethylphenyl)-pyrazole |

EXAMPLE 134

3-(2-Carboxy-1-cyclohexen-1-yl)-5-(4-methoxyphenyl)-pyrazole was dissolved in hot water, treated with sodium hydroxide solution, and cooled to 5° to give a precipitate of 3-(2-carboxy-1-cyclohexen-1-yl)-5-(4-methoxyphenyl)pyrazole, sodium salt.

By the procedure of Example 134, using 3-(2-carboxy-1-cyclohexen-1yl)-5-phenylpyrazole and the indicated reactant, the following salts are prepared.

| Ex. No. | Reactant | Product |
|---|---|---|
| 135 | LiOH | 3-(2-carboxy-1-cyclohexen-1-yl)-5-phenylpyrazole, lithium salt |
| 136 | KOH | 3-(2-carboxy-1-cyclohexen-1-yl)-5-phenylpyrazole, potassium salt |
| 137 | Ca(OH)$_2$ | 3-(2-carboxy-1-cyclohexen-1-yl)-5-phenylpyrazole, calcium salt |
| 138 | (CH$_3$)$_4$N$^+$OH$^-$ | 3-(2-carboxy-1-cyclohexen-1-yl)-5-phenylpyrazole, tetramethylammonium salt |
| 139 | (CH$_3$)$_3$N, H$_2$O | 3-(2-carboxy-1-cyclohexen-1-yl)-5-phenylpyrazole, trimethylammonium salt |
| 140 | (CH$_3$)$_2$NH, H$_2$O | 3-(2-carboxy-1-cyclohexen-1-yl)-5-phenylpyrazole, dimethylammonium salt |
| 141 | CH$_3$NH$_2$, H$_2$O | 3-(2-carboxy-1-cyclohexen-1-yl)-5-phenylpyrazole, methylammonium salt |
| 142 | C$_{12}$H$_{25}$NH$_2$, H$_2$O | 3-(2-carboxy-1-cyclohexen-1-yl)-5-phenylpyrazole, dodecylammonium salt |
| 143 | (C$_4$H$_9$)$_4$N$^+$OH$^-$ | 3-(2-carboxy-1-cyclohexen-1-yl)-5-phenylpyrazole, tetrabutylammonium salt |

EXAMPLE 144

3-(2-Carbomethoxy-1-cyclohexen-1-yl)-5-phenylpyrazole is dissolved in ether and treated with gaseous hydrogen chlorides to precipitate 3-(2-carbomethoxy-1-cyclohexen-1-yl)-5-phenylpyrazole hydrochloride.

By substitution of 100% phosphoric, sulfuric, or nitric acid for hydrogen chloride of Example 144, the following products are generated.

| Ex. No. | Acid | Product |
|---|---|---|
| 145 | phosphoric acid | 3-(2-carboethoxy-1-cyclohexen-1-yl)-5-phenylpyrazole, phosphoric acid salt |
| 146 | sulfuric acid | 3-(2-carboethoxy-1-cyclohexen-1-yl)-5-phenylpyrazole, sulfuric acid salt |
| 147 | nitric acid | 3-(2-caroethoxy-1-cyclohexen-1-yl)-5-phenylpyrazole, nitric acid salt |

EXAMPLE 148

A mixture of 3.0 g 3-(2-carbomethoxy-1-cyclohexen-1-yl)-5-phenylpyrazole, 0.3 g of 50% sodium hydride-mineral oil slurry, and 1.0 g of methyl iodide in 50 ml of anhydrous tetrahydrofuran is stirred and refluxed overnite. The reaction mixture is filtered, and the solvent is evaporated from the filtrate to give 1-methyl-3-(2-carbomethoxy-1-cyclohexen-1-yl)-5-phenylpyrazole.

Using the indicated reactants instead of methyl iodide with 3-(2-carbomethoxy-1-cyclohexen-1-yl)-5-phenylpyrazole in the procedure of Example 148, the following pyrazoles are prepared.

| Ex. No. | Reactant | Product |
|---|---|---|
| 149 | (CH$_3$)$_2$CHCH$_2$Br | 1-isobutyl-3-(2-carbomethoxy-1-cyclohexen-1-yl)-5-phenylpyrazole |
| 150 | CH$_3$CH$_2$I | 1-ethyl-3-(2-carbomethoxy-1-cyclohexen-1-yl)-5-phenylpyrazole |
| 151 | CH$_3$COCl | 1-acetyl-3-(2-carbomethoxy-1-cyclohexen-1-yl)-5-phenylpyrazole |
| 152 | C$_2$H$_5$OCOCl | 1-ethoxycarbonyl-3-(2-carbomethoxy-1-cyclohexen-1-yl)-5-phenylpyrazole |
| 153 | (CH$_3$)$_2$CHCH$_2$OCOCl | 1-isobutyoxycarbonyl-3-(2-carbomethoxy-1-cyclohexen-1-yl)-5-phenylpyrazole |
| 154 | 3,4-dimethylphenylsulfonyl chloride | 1-(3,4-dimethylphenylsulfonyl)-3-(2-carbomethoxy-1-cyclohexen-1-yl)-5-phenylpyrazole |

By the procedure of Example 106, using 1,2,3,6-tetrahydrophthalic anhydride and the ketones shown, the following pyrazoles are prepared.

| Ex. No. | Ketone | Product | Melting Point |
|---|---|---|---|
| 155 | acetophenone | 6-(3-phenyl-5-pyrazolyl)-3-cyclohexene-1-carboxylic acid | 114–116° |
| 156 | 3-methyl-2-butanone | 6-(3-i-propyl-5-pyrazolyl)-3-cyclohexene-1-carboxylic acid | |
| 157 | 3-ethyl-2-hexanone | 6-[3-(1-ethylbutyl)-5-pyrazolyl]-3-cyclohexene-1-carboxylic acid | |
| 158 | 3,3-dimethyl-2-hexanone | 6-[3-(1,1-dimethylbutyl)-5-pyrazolyl]-3-cyclohexene-1-carboxylic acid | |
| 159 | methyl cyclopentyl ketone | 6-(3-cyclopentyl-5-pyrazolyl)-3-cyclohexene-1-carboxylic acid | |
| 160 | 4-methoxyacetophenone | 6-[3-(4-methoxyphenyl)-5-pyrazolyl]-3-cyclohexene-1-carboxylic acid | |
| 161 | 4-methylacetophenone | 6-[3-(4-methylphenyl)-5-pyrazolyl]-3-cyclohexene-1-carboxylic acid | |
| 162 | 4-chloroacetophenone | 6-[3-(4-chlorophenyl)-5-pyrazolyl]-3-cyclohexene-1-carboxylic acid | |

By the procedure of Example 106, using 7-oxabicyclo[2.2.1]hept-5-ene-2,3-dicarboxylic anhydride and the ketones shown, the following pyrazoles are prepared.

| Ex. No. | Ketone | Product |
|---|---|---|
| 163 | acetophenone | 3-(3-phenyl-5-pyrazolyl)-7-oxabicyclo[2.2.1]hept-5-ene-2-carboxylic acid |
| 164 | 4-methylacetophenone | 3-[3-(4-methylphenyl)-5-pyrazolyl]-7-oxabicyclo[2.2.1]hept-5-ene-2-carboxylic acid |
| 165 | 4-chloroacetophenone | 3-[3-(4-chlorophenyl)-5-pyrazolyl]-7-oxabicyclo[2.2.1]hept-5-ene-2-carboxylic acid |
| 166 | 4-methoxyacetophenone | 3-[3-(4-methoxyphenyl)-5-pyrazolyl]-7-oxabicyclo[2.2.1]hept-5-ene-2-carboxylic acid |

1. A composition which kills or retards the growth of undesired vegetation or beneficially modifies the growth of desired plants consisting essentially of an inert diluent and an effective amount of a compound of the formula

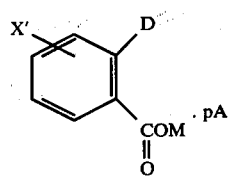

wherein D is

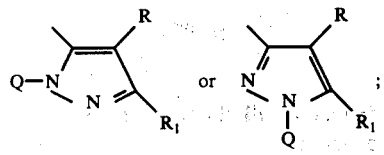

X' is hydrogen, fluorine, chlorine, bromine or methyl;
R is hydrogen or a group selected from —CH$_2$—, —CH$_2$CH$_2$—, and
—CH=CH— which joins the 4-position of the pyrazole ring with the 2-position of the R$_1$ substituent;
R$_1$ is sec-alkyl of three to six carbon atoms; tert-alkyl of four to six carbon atoms, cycloalkyl of five or six carbon atoms, naphthyl, biphenylyl, or

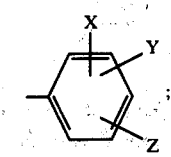

X is hydrogen, halogen, alkyl of one to four carbon atoms, hydroxy, alkoxy of one to four carbon atoms, alkylthio of one to four carbon atoms, alkysulfonyl of one to four carbon atoms, trifluoromethyl or nitro;

Y is hydrogen, chlorine, bromine, methoxy or methyl; and
Z is hydrogen, chlorine, or methyl;
Q is hydrogen, alkyl of one to four carbon atoms, alkanoyl of one to four carbon atoms, alkoxycarbonyl of two to five carbon atoms, or benzensulfonyl optionally substituted with chlorine or one of two methyls
M is hydrogen, benzyl, alkyl of one to six carbon atoms, hydroxyalkyl of two or three carbon atoms, alkoxyalkyl of three to five carbon atoms, sodium, potassium, lithium, calcium, magnesium, or

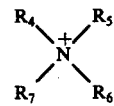

where
R$_4$, R$_5$ and R$_6$ are each independently hydrogen, alkyl of one to four carbon atoms or hydroxyalkyl of two to four carbon atoms; and
R$_7$ is hydrogen, alkyl of one to twelve carbon atoms or benzyl;
p is 0 or 1; and
A is HCl, H$_2$SO$_4$, HNO$_3$ and H$_3$PO$_4$
with the provisos that:
1. when M is other than hydrogen, benzyl or optionally substituted alkyl, p is O; and
2. the total number of carbon atoms in X, Y, and Z cannot exceed 4.

2. A composition of claim 1 wherein R$_1$ is p-methoxyphenyl, p-tolyl, p-chlorophenyl, or phenyl.

3. The composition of claim 1 wherein said compound is 2-(4,5-dihydro-7-methoxy-2H-benz-[g]-indazol-3-yl)-benzoic acid having the formula:

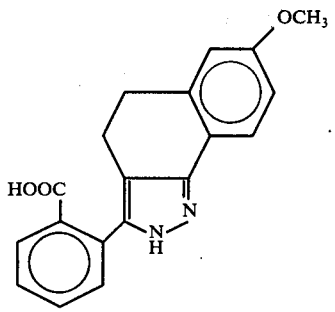

4. A composition which kills or retards the growth of undesired vegetation or beneficially modifies the growth of desired plants consisting essentially of an inert diluent and an effective amount of a compound of the formula

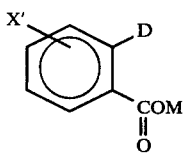

wherein
D is

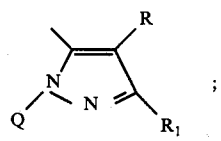

M is hydrogen or alkyl of one to six carbon atoms;
X' is hydrogen;
R is a group selected from —CH$_2$—, —CH$_2$CH$_2$— and —CH=CH— which joins the 4-position of the pyrazole ring with the 2-position of the R$_1$ substituent;
R$_1$ is

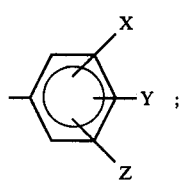

X is hydrogen or alkoxy of one to four carbon atoms; and each of Q, Y and Z is hydrogen.

5. The composition of claim 4 wherein R is —CH$_2$—.
6. The composition of claim 4 wherein R is —CH$_2$CH$_2$—.
7. The composition of claim 4 wherein R is —CH=CH—.
8. The composition of claim 4 wherein M is hydrogen.
9. The composition of claim 4 wherein M is alkyl of one to six carbon atoms.
10. The composition of claim 4 wherein X is hydrogen.
11. The composition of claim 4 wherein X is alkoxy of one to four carbon atoms.

12. The composition of claim 4 wherein said compound is 2-(7-methoxy-2H-benz[g]indazol-3-yl(benzoic acid having the formula

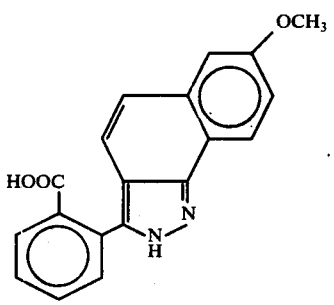

13. A method of killing or retarding the growth of undesired vegetation or beneficially modifying the growth of desired plants consisting essentially of applying to the plant an effective amount of a compound of claim 1.

14. A method of claim 13 wherein R$_1$ is p-methoxyphenyl, p-tolyl, p-chlorophenyl or phenyl.

15. A method of killing or retarding the growth of undesired vegetation or beneficially modifying the growth of desired plants consisting essentially of applying to the plant an effective amount of a compound of the formula:

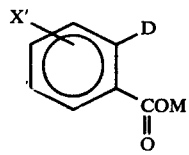

wherein
D is

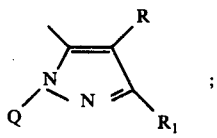

M is hydrogen or alkyl of one to six carbon atoms;
X' is hydrogen;
R is a group selected from —CH$_2$—, —CH$_2$CH$_2$—and —CH=CH which joins the 4-position of the pyrazole ring with the 2-position of the R$_1$ substituent;
R$_1$ is

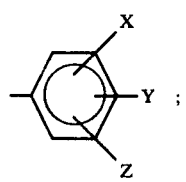

X is hydrogen or alkoxy of one to four carbon atoms; and each of Q Y and Z is hydrogen.

16. The method of claim 15 wherein said compound is 2(4,5-dihydro-7-methoxy-2H-benz-[g]-indazol-3-yl)-benzoic acid having the formula:

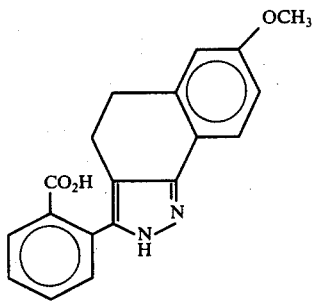

17. The method of claim 15 wherein R is —CH₂—.
18. The method of claim 15 wherein R is —CH₂CH₂—.
19. The method of claim 15 wherein R is —CH═CH—.
20. The method of claim 15 wherein M is hydrogen.
21. The method of claim 15 wherein M is alkyl of 1 to six carbon atoms.
22. The method of claim 15 wherein X is hydrogen.
23. The method of claim 15 wherein X is alkoxy of one to four carbon atoms.
24. The method of claim 15 wherein said compound is 2-(7-methoxy-2H-benz[g]indazol-3-yl)benzoic acid having the formula

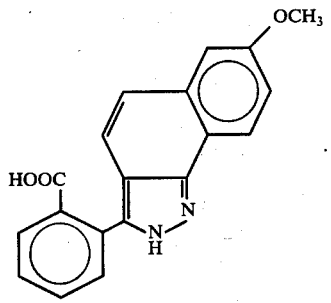

* * * * *

UNITED STATES PATENT OFFICE
CERTIFICATE OF CORRECTION

PATENT NO. : 4,055,409
DATED : October 25, 1977
INVENTOR(S) : Johnson et al.

It is certified that error appears in the above-identified patent and that said Letters Patent are hereby corrected as shown below:

| Column | Line(s) | |
|---|---|---|
| 26 | 38 | "benzensulfo" should be -- benzenesulfo- --. |
| 26 | 40 | after "methyls" there should be a -- ; --. |
| 26 | 58 | "and" should be -- or --. |
| 27 | 58 | "-CH=●" should be -- -CH=CH- --. |
| 28 | 51 | "-CH=CH" should be -- -CH=CH- --. |
| 28 | 65 | "Q Y" should be -- Q, Y --. |
| 29 | 20 | "-CH=●" should be -- -CH=CH- --. |

Signed and Sealed this

Seventh Day of March 1978

[SEAL]

Attest:

RUTH C. MASON
Attesting Officer

LUTRELLE F. PARKER
Acting Commissioner of Patents and Trademarks